(12) United States Patent
Binnekamp et al.

(10) Patent No.: US 10,092,778 B2
(45) Date of Patent: Oct. 9, 2018

(54) TREATMENT DEVICE AND A TREATMENT SYSTEM

(71) Applicant: KONINKLIJKE PHILIPS N.V., Eindhoven (NL)

(72) Inventors: Dirk Binnekamp, Borne (NL); Leonardus Jozef Lucas Maria Koch, Eindhoven (NL); Funda Sahin Nomaler, Eindhoven (NL); Aditya Mehendale, Geldrop (NL); Maurice Hubertus Elisabeth Van Der Beek, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 331 days.

(21) Appl. No.: 14/430,326

(22) PCT Filed: Sep. 12, 2013

(86) PCT No.: PCT/IB2013/058487
§ 371 (c)(1),
(2) Date: Mar. 23, 2015

(87) PCT Pub. No.: WO2014/049477
PCT Pub. Date: Apr. 3, 2014

(65) Prior Publication Data
US 2015/0246247 A1 Sep. 3, 2015

Related U.S. Application Data

(60) Provisional application No. 61/705,196, filed on Sep. 25, 2012.

(51) Int. Cl.
*A61N 5/10* (2006.01)
*A61B 18/24* (2006.01)
(Continued)

(52) U.S. Cl.
CPC ......... *A61N 5/1075* (2013.01); *A61N 5/1007* (2013.01); *A61N 5/1027* (2013.01);
(Continued)

(58) Field of Classification Search
CPC .. A61N 5/1007–5/1027; A61N 5/1048; A61N 5/1075
See application file for complete search history.

(56) References Cited

U.S. PATENT DOCUMENTS

| 6,337,627 B1 | 1/2002 | Von Gutfeld et al. |
| 6,447,438 B1 | 9/2002 | Bernardi et al. |

(Continued)

FOREIGN PATENT DOCUMENTS

| JP | S4843483 A | 6/1973 |
| WO | 0187400 A1 | 11/2001 |

(Continued)

*Primary Examiner* — Thaddeus Cox

(57) ABSTRACT

A treatment device (100) and a treatment system are provided. The treatment device (100) is suitable for temporarily or permanently placing a therapeutic device (112) in a part of a corpus of a living being. The treatment device (100) comprises an elongated body (102) for being inserted in the part of the corpus. The elongated body (102) comprises a channel (110) and an impedance sensor element (104). The channel (110) is for guiding the therapeutic device (112) to a specific position (PI) within the channel (110) and/or for holding the therapeutic device (112) at a specific position (PI) within the channel (110). The impedance sensor element (1040) is configured to be coupled to a detection device for detecting the presence of the therapeutic device (112) at the specific position (PI) on basis of a change of a signal provided by the impedance sensor element (104).

13 Claims, 4 Drawing Sheets

(51) Int. Cl.
*A61B 18/00* (2006.01)
*A61B 90/00* (2016.01)

(52) U.S. Cl.
CPC ..... *A61B 18/24* (2013.01); *A61B 2018/00196* (2013.01); *A61B 2018/00547* (2013.01); *A61B 2090/062* (2016.02); *A61B 2090/3954* (2016.02); *A61N 5/1001* (2013.01); *A61N 5/1048* (2013.01); *A61N 2005/1024* (2013.01)

(56) References Cited

U.S. PATENT DOCUMENTS

| | | | |
|---|---|---|---|
| 6,847,838 B1 | 1/2005 | Macey et al. | |
| 9,364,685 B2 | 6/2016 | Kindlein | |
| 9,733,336 B2 | 8/2017 | Shen et al. | |
| 2007/0043291 A1* | 2/2007 | Fidel | A61B 8/12 600/439 |
| 2007/0118009 A1* | 5/2007 | Hoheisel | A61B 5/064 600/3 |
| 2007/0285248 A1 | 12/2007 | Hamel et al. | |
| 2008/0140006 A1* | 6/2008 | Eskuri | A61B 5/00 604/117 |
| 2009/0299124 A1* | 12/2009 | Francescatti | A61N 5/1015 600/3 |
| 2011/0207987 A1* | 8/2011 | DiCarlo | A61N 5/1017 600/3 |
| 2012/0022314 A1* | 1/2012 | Sing | A61B 90/39 600/3 |
| 2013/0035537 A1* | 2/2013 | Wallace | A61B 34/30 600/8 |
| 2015/0246247 A1 | 9/2015 | Binnekamp et al. | |

FOREIGN PATENT DOCUMENTS

| | | |
|---|---|---|
| WO | 2006016368 A2 | 2/2006 |
| WO | 2008073214 A2 | 6/2008 |
| WO | 2011053908 A1 | 5/2011 |
| WO | 2011080606 A1 | 7/2011 |

* cited by examiner

TREATMENT DEVICE AND A TREATMENT SYSTEM

CROSS-REFERENCE TO PRIOR APPLICATIONS

This application is the U.S. National Phase application under 35 U.S.C. § 371 of International Application No. PCT/IB2013/058487, filed on Sep. 12, 2013, which claims the benefit of U.S. Provisional Patent Application No. 61/705,196, filed on Sep. 25, 2012. These applications are hereby incorporated by reference herein.

FIELD OF THE INVENTION

The invention relates to a treatment device for temporarily or permanently placing a therapeutic device in a part of a corpus of a living being. The invention further relates to a treatment system comprising the treatment device.

BACKGROUND OF THE INVENTION

In brachytherapy, and especially in in-vivo brachytherapy, a radiation source is placed within the body at a position within or next to a tissue requiring radiation treatment. Several forms of cancer, such as prostate cancer, are treated with brachytherapy. In these forms of treatment it is important that the radiation source is placed at a predetermined position within the corpus to obtain the most effective treatment of the cancerous tissue. If the radiation source is not placed at the correct position, the tissues could potentially receive wrong radiation doses leading to under-dosing and/or overdosing affecting the efficacy of the treatment.

In an example, the energy emitting sources may be a radioactive source. Some of the sources emit a relatively low amount of energy (in the so-termed low-dose rate brachytherapy) and are placed permanently within the body by means of, for example, a needle. Some of the energy emitting sources emit a relatively large amount of energy (in the so-termed high-dose rate brachytherapy) and are temporarily placed at a specific position next to the tissue to be treated in, for example, a catheter. In high-dose rate brachytherapy the radiation source is, for example, coupled to a wire and the radiation source is fired into the catheter to a predefined position which relates to the length of the wire. Research has shown that in these embodiments of high-dose rate brachytherapy the radiation source does not always reach the predefined position. There is a need for an independent check of the position of the radiation source within the catheter.

Also in other forms of therapy an energy emitting source is guided through a probe, needle or, for example, a catheter into the corpus. In these forms of therapy it is also required to know the exact position of an energy emitting source within the body. An example of such therapeutic technique is laser induced thermal therapy wherein an optical fiber is inserted through a probe into a tumor and laser light is guided to the tip of the optical fiber. In laser induced thermal therapy it is not only important to know whether the optical fiber reached the tip of the probe and where the probe-tip actually is, but it is also important to know how much the optical fiber protrudes out of the probe. Thus, it is required to have an independent check to determine the relative position of the optical fiber with respect to the probe.

Published patent application U.S. Pat. No. 6,447,438 relates to an apparatus and method for locating therapeutic seeds implanted in the human body. The disclosure relates to low-dose rate brachytherapy for treating prostate cancer. In such a therapy, energy emitting therapeutic seeds are implanted in the prostate via needle. Prior to the treatment a treatment plan is made which prescribes the position of the treatment seeds within the prostrate. In practice it is relatively difficult to be sure about the position where the therapeutic seeds are implanted in the prostate and the efficacy of the treatment decreases if the seeds are implanted at another position than the prescribed position. The cited patent application provides an apparatus and a method which may be used to locate already implanted therapeutic seeds. This information may be used, during the process of implanting the therapeutic seeds, to update the treatment plan. According to the provided reference, the therapeutic seeds are partially ferromagnetic and are caused to vibrate by a magnetic field and the vibrating therapeutic seeds are identified by reflections of ultrasonic signals transmitted to the therapeutic seeds. The information provided by the apparatus and the method of the cited reference relates to already implanted therapeutic seeds and does not relate to a position of a seed just before the actual moment of implantation. Thus, the apparatus and the method may be useful in the context of updating the treatment plan, but do not help a surgeon in implanting the seeds at the predefined positions.

SUMMARY OF THE INVENTION

It is an object of the invention to provide a treatment device which provides an independent check of a position of an energy emitting therapeutic device with respect to the position of the treatment device.

A first aspect of the invention provides a treatment device. A second aspect of the invention provides a treatment system. Advantageous embodiments are defined in the dependent claims.

A treatment device in accordance with the first aspect of the invention is suitable for temporarily or permanently placing a therapeutic device in a part of a corpus of a living being. The treatment device comprises an elongated body for being inserted in the part of the corpus. The elongated body comprises a channel and an impedance sensor element. The channel is for guiding the therapeutic device to a specific position within the channel and/or for holding the therapeutic device at a specific position within the channel. The impedance sensor element is configured to be coupled to a detection device for detecting the presence of the therapeutic device at the specific position on basis of a change of a signal provided by the impedance sensor element.

The treatment device is suitable for placing a therapeutic device at a position in a corpus. The elongated body with the channel is the means by which the therapeutic device is positioned within the corpus—the channel guides the therapeutic device to a required position. The therapeutic device may be pushed into, blown through, fired into or pulled through the channel to the required position. To permanently implant the therapeutic device into the corpus, the therapeutic device may be pushed out of the channel and/or the elongated body is pulled back while at the same moment in time the therapeutic device is kept at its position in the corpus by, for example, a plunger. If the therapeutic device has to be present at the specific position only for a limited interval of time, the elongated body is pulled back after the interval of time, or the therapeutic device is guided, via the channel, out of the corpus after the limited interval of time.

The treatment device comprises the impedance sensor element which is capable to detect the presence of the therapeutic device at the specific location. The impedance sensor element at least provides a signal which changes when the object arrives at or moves away from the specific location. In an example, the impedance (such as its capacitance, inductance, or resistance) of the impedance sensor element changes in response to the presence of the therapeutic device at the specific location. In another example, the impedance sensor element uses a transformer-action, such as linear variable differential transformer (LVDT) to generate the signal. The therapeutic device may, for example, comprise a metal which influences the inductance or capacitance of the impedance sensor element. When the impedance sensor element uses a transformer action, metal or a ferromagnetic being present in the therapeutic device influences the transformer action. Thus, when the therapeutic device is present at the specific position, the signal provided by the impedance sensor element changes and if the change is detected, accurate position information about the therapeutic device is obtained. The actual detection of the change of the signal is performed by a detection device which provides information to, for example, a surgeon. The impedance sensor element is at least configured to be coupled to the detection device, for example, by means of wires.

Thus, if the therapeutic device has to be permanently implanted in the corpus it is advantageous to know that the therapeutic device is, for example, present at a tip of the elongated body where, for example, an exit of the channel is available such that, when a force is applied to release therapeutic device, it is known that the therapeutic device is released immediately. If the therapeutic device has to stay for a limited amount of time in the part of the corpus, it is advantageous to know whether the therapeutic device is exactly present at the specific position within the channel to prevent, for example, that tissues are irradiated which shouldn't be irradiated when the therapeutic device is an energy radiating therapeutic device. It is to be noted that specific imaging techniques or other tracking technologies may be simultaneously or independently used to detect whether the elongated body is present at the correct position within the part of the corpus. Because of various reasons, these techniques are often not suitable to detect continuously whether the therapeutic device is present at the specific position within the channel. Therefore, the treatment device provides an additional check to be sure that the therapeutic device is present at the specific position within the channel.

It is to be noted that the therapeutic device may be a passive object which emits energy in the form of, for example, X-ray. The therapeutic device may also be device which emits light, or an object which releases medicines, or, in an alternative embodiment, the therapeutic device is a surgical tool, such as a biopsy tool which takes tissue samples to determine the pathological status of the tissue. It is further to be noted that the term "the specific position" does not only mean "a specific point", but may in the context of this document also be read as "a specific region". In practical embodiments, the signal provided by the impedance sensor element may change when the therapeutic device is present in the specific region.

Optionally, the therapeutic device comprises an energy emitting therapeutic device.

Optionally, the impedance sensor element is configured to be coupled to an impedance detection device for detecting a change of impedance of the impedance sensor element in response to the presence of the therapeutic device at the specific position.

Optionally, the impedance sensor element comprises a coil for detecting an electromagnetic field at the specific position. Coils are effective means to detect electromagnetic fields. If the coil is arranged at or close to the specific position, it is capable of measuring an electromagnetic field at the specific position. If the therapeutic device is present at the specific position, the electromagnetic field changes compared to a situation without the therapeutic device, and the coil is capable of measuring such a change.

In an optional embodiment, the electromagnetic field is generated by the coil Itself—the coil may be connected to a signal generator which applies an AC voltage to the coil. If the coil receives an AC voltage, its inductance may be measured and when a therapeutic device, which comprises, for example, at least some metal, is present in or near the coil, the measured inductance differs in comparison to a situation in which the therapeutic device is absent.

In another optional embodiment, the coil comprises a ferrite core. A coil with a ferrite core is better capable in detecting an electromagnetic field.

Optionally, the coil is arranged around the channel. Thus, if the therapeutic device is present in a portion of the channel which is enclosed by the coil, or which is near the coil, the coil measures a different electromagnetic field compared to a situation that the therapeutic device is not present at the specific location. A further advantage of the use of a coil is that, when the coil is made out of thin wires, the thickness of the elongated body measured in a direction perpendicular to the channel, is only slightly increased due to the presence of the coil. This is especially advantageous in in-vivo surgery because inserting thinner elongated objects into the part of the corpus has less impact on the part of the corpus.

Optionally, the elongated body comprises a needle, probe, a trocar, a cannula or a catheter. Needles, probes, trocars, cannulas and catheters are elongated bodies with a channel which may be used for in-vivo brachytherapy.

Optionally, the elongated body comprises a further impedance sensor element to be coupled to the detection device for detecting, in collaboration with a detection via the impedance sensor element, the presence of the therapeutic device at the specific position on basis of a change of a signal provided by the impedance sensor element and/or provided by the further impedance sensor element. When two impedance sensor elements are present, more accurate position information about the therapeutic device may be obtained. Furthermore, if two impedance sensor elements are used, the combination is probably more sensitive and/or a larger change in the signal may be obtained in response to the presence of the therapeutic device at the specific location.

Optionally, the further impedance sensor element comprises a further coil being arranged around the channel for detecting the electromagnetic field at the specific position. Previously discussed advantages of using the coil as a part of the impedance sensor element apply also to this optional embodiment.

Optionally, at least one of the impedance sensor element and the further impedance sensor element is configured to also detect an electromagnetic field being generated by a field generator which is arranged at a fixed position with respect to the corpus. The at least one of the impedance sensor element and the further impedance sensor element is also configured to be coupled to a position tracking device for tracking a relative position of the at least one of the impedance sensor element and the further impedance sensor element with respect to the fixed position. Thus, the impedance sensor element and/or the further impedance sensor element may have a second detection function. They do not only have the function of detecting a position of the therapeutic element within the channel of the elongated body, but they may also be used in ElectroMagnetic tracking systems which are used to track a position of the sensor element with respect to a fixed, known, position in, for example, the operating theater—and, thus, to track a position of the sensor element within the corpus (assuming that the position of the corpus with respect to the fixed position is well known). Specific position tracking devices may be coupled to at least one of the impedance sensor element and the further impedance sensor element and the position tracking devices may be coupled to imaging system which displays the position of at least one of the impedance sensor element and the further impedance sensor element within the corpus to, for example, a surgeon.

Alternatively, the treatment device comprises another coil. The another coil is electrically isolated from the impedance sensor element and the another coil is configured to detect an electromagnetic field being generated by a field generator which is arranged at a fixed position with respect to the corpus. The another coil is configured to be coupled to a position tracking system for tracking a position of the another coil with respect to the fixed position. In specific embodiments it may be useful not to use one of the impedance sensor element and the further impedance sensor element to track the position of the elongated body within the corpus. For example, it may be advantageous to place the another coil at another portion of the elongated body than the impedance sensor element and/or the further impedance sensor element. For example, the another coil may be positioned at a tip of a catheter such that, for example, a surgeon may track whether the catheter was inserted far enough within the urethra and the impedance sensor element and/or the further impedance sensor element may be used to detect that, for example, a high-dose rate therapeutic device is present at a predefined distance away from the tip of the catheter to treat, for example, prostate cancer.

Optionally, the treatment device further comprises an excitation source which generates an AC voltage. The impedance sensor element, the further impedance sensor element and the excitation source are arranged in a bridge configuration. The bridge configuration comprises a first terminal, a second terminal, a third terminal, a fourth terminal, a first load resistor and a second load resistor. The first load resistor is arranged between the second terminal and the fourth terminal. The second load resistor is arranged between the third terminal and the fourth terminal. The second load resistor and the first load resistor balance a load of each one of two current conduction paths of the bridge configuration. The excitation source is arranged between the first terminal and the fourth terminal. The impedance sensor element is arranged between the first terminal and the second terminal. The further impedance sensor element is arranged between the first terminal and the third terminal. One or more detection devices may be coupled to the second terminal and the third terminal.

According to this optional embodiment the respective sensor element, the load resistor and the excitation source are arranged in the so-termed bridge configuration. In this bridge configuration the signal generated by the excitation source is provided, via the respective load resistors and the two current conduction paths, to both impedance sensor elements. The generated AC signal is used to generate, in the impedance sensor elements, an electromagnetic field which changes under the influence of the presence of a therapeutic device. Such a change of the electromagnetic field changes the voltage of the terminals to which the detection devices may be coupled. The detection devices are coupled to two terminals which are in between the respective sensor elements and the respective load resistors and this configuration has specific advantages. First of all it is possible to detect the relative impedance of the impedance sensor element with respect to the further impedance sensor element instead of measuring an absolute impedance. Thus, the detected relative impedance is a signal around the value of zero. It is often easier to interpret and process a signal around zero. In addition to this, the polarity of the measured impedance may indicate whether the therapeutic device is closer to the impedance sensor element than to the further impedance element (and vice versa) resulting in a more accurate position information. Furthermore, in the bridge configuration orthogonal axes are used for actuation (by the excitation source) and the sensing (by the detection device(s)). It makes it easier, in the detection devices, to distinguish between signals which relate to the excitation source (and, thus, relate to the impedance of the impedance sensor element), and signals detected by the series arrangement of impedance sensor elements which relate to an externally generated electromagnetic field which is used for tracking a position of the sensor element with respect to a fixed position of a field generator generating the external electromagnetic field. The signal received from the excitation source is often relatively large and the signal related to the externally generated electromagnetic field is usually relatively small.

It is to be noted that the applied AC voltage is a signal which alternates between a positive and a negative voltage. A specific waveform of the AC voltage is not important. In the context of this document, an AC voltage may have a sine waveform, a saw tooth waveform, a square waveform or a triangle waveform.

According to a second aspect, a treatment system for treating a part of a corpus of a living being is provided. The treatment system comprises a treatment device according to the first aspect of the invention and a detection device. Optional embodiments of the treatment device have been discussed above. The treatment device is configured for temporarily or permanently placing a therapeutic device in a part of a corpus of a living being. The detection device is configured to be connected to the impedance sensor element of the treatment device and is configured to detect a change of the signal provided by the impedance sensor element in response to the presence of the therapeutic device at the specific position.

The treatment system according to the second aspect of the invention provides the same benefits as the treatment device according to the first aspect of the invention and has similar embodiments with similar effects as the corresponding embodiments of the system.

Optionally, the treatment system further comprises an excitation source for generating an AC voltage which is provided to the impedance sensor element of the treatment device. The detection device comprises a synchronous detection system which is synchronized with the excitation source. Such a configuration is a configuration for measuring the impedance of the impedance sensor element. If the therapeutic device is present at the specific position, the impedance of the impedance sensor element changes and the signal provided by the impedance sensor element changes. When the impedance sensor element is a coil, this configuration senses the inductance of the coil.

Synchronous detection inherently rejects information at all frequencies (and optionally even phases) other than the frequency (and phase) of the applied or generated AC voltage. This offers, in specific application a perfect rejection of other electromagnetic signals being present in the environment of the treatment system. As discussed in other embodiments, an externally applied electromagnetic field may be present and the synchronous detection system rejects this signal as long as it has another frequency and/or phase than the applied AC voltage.

Optionally, the treatment system further comprises a tracking device connectable to the impedance sensor element of the treatment device for tracking a relative position of the impedance sensor element with respect to a fixed position of a field generator. The field generator generates an electromagnetic field which is detectable by the impedance sensor element. As discussed previously, the impedance sensor elements may also be used to track a position of the impedance sensor elements within the corpus by means of the features provided in this optional embodiment. This is advantageous if, for example, a surgeon has to be sure of the position of the treatment device within the corpus.

Optionally, the treatment system further comprises a filter coupled between the impedance sensor element at one end and the impedance detection device and the tracking device at another end. The filter filters a signal from the impedance sensor element into a first signal component, which comprises impedance information related to the presence of the therapeutic device at the specific position, and a second signal component, which comprises tracking information related to the relative position of the impedance sensor element with respect to the fixed position of the field generator. If the filter subdivides the signal received from the impedance sensor element into different signal components which comprise specific types of information, the overall signal to noise ratio per signal component may be reduced which allows the devices, which have to process the signal components, to process the information more accurately.

Optionally, the treatment system further comprises the energy emitting therapeutic device.

The therapeutic device may be an energy emitting therapeutic device which radiates any suitable form of energy for treating the part of the corpus. The form of energy may, for example, be heat, cold, light, or energy radiated by nuclear material. The therapeutic device is suitable for being used in combination with the treatment device, which means that the therapeutic device is at least small enough to be guided through the channel of the elongated body. Depending on the specific technology used to get the therapeutic device at the specific position, the therapeutic device needs to have the same diameter as the channel, or therapeutic device may be smaller, but must, in an example, be coupled to a wire which is used to pull back the therapeutic device.

Optionally, the therapeutic device is an energy emitting therapeutic device which comprises low-dose rate therapeutic seeds. Low-dose rate therapeutic seeds are, in particular, used for permanent implantation in the treated part of the corpus. In specific treatments with low-dose rate therapeutic seeds, it is relatively difficult to be sure that the low-dose rate therapeutic seeds are released at the predefined position within the treated part of the corpus during the process of implanting the seeds. The treatment system according to this optional embodiment provides, for example, the surgeon with additional information which helps him to increase the accuracy of the placement of the low-dose rate therapeutic seeds in the treated part of the corpus. It is to be noted that this advantage does not only relate to low-dose rate therapeutic seeds, but also related to treatments with other energy radiation therapeutic devices.

Optionally, the energy emitting therapeutic device comprises an optical fiber for guiding energy in the form of light into the part of the corpus. The, the optical fiber comprises a reference element being arranged at a predefined position at the optical fiber, and wherein the impedance sensor element is configured to detect the presence of the reference element at the specific position. Thus, the reference element influences the signal that is provided by the impedance sensor element to the detection device. If the reference element has a predefined position at the optical fiber and the reference element is detected at the specific position, the relative position of the optical fiber with respect to the position of the elongated body known. For example, it is known whether a top of the optical fiber protrudes far enough out of the channel of the elongated object. In an exemplary embodiment, the impedance sensor element is a coil arranged around the channel of the treatment device at the specific position, the reference element is a metal ring arranged around the optical fiber, and the inductance of the coil changes if the reference element is at the specific position.

These and other aspects of the invention are apparent from and will be elucidated with reference to the embodiments described hereinafter.

It will be appreciated by those skilled in the art that two or more of the above-mentioned options, implementations, and/or aspects of the invention may be combined in any way deemed useful.

Modifications and variations of the device and/or system, which correspond to the described modifications and variations of the device, can be carried out by a person skilled in the art on the basis of the present description.

Figure 1A:
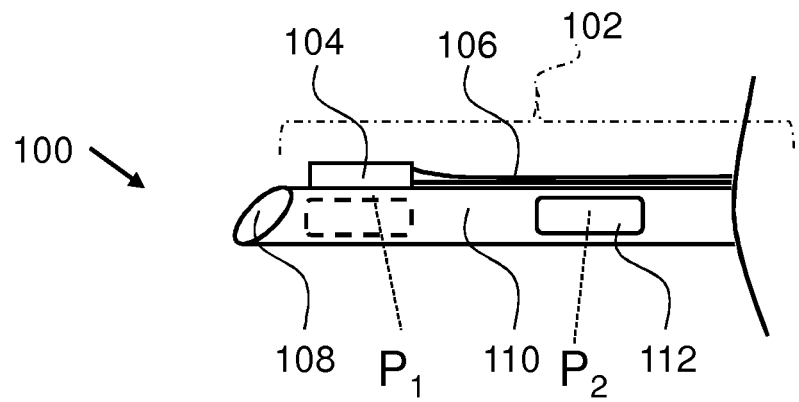
FIG. 1a schematically shows an embodiment of a treatment device according to the first aspect of the invention, FIG. 1b schematically shows another embodiment of a treatment device, FIG. 1c schematically shows a further embodiment of a treatment device, FIG. 2 schematically shows an embodiment of a treatment system according to the second aspect of the invention, FIG. 3 schematically shows another embodiment of a treatment system, FIG. 4 schematically shows a further embodiment of a treatment system.

It should be noted that items denoted by the same reference numerals in different Figures have the same structural features and the same functions, or are the same signals. Where the function and/or structure of such an item have been explained, there is no necessity for repeated explanation thereof in the detailed description.

The Figures are purely diagrammatic and not drawn to scale. Particularly for clarity, some dimensions are exaggerated strongly.

DETAILED DESCRIPTION

A first embodiment is shown in FIG. 1a. FIG. 1a schematically shows a treatment device 100 which comprises an elongated body 102. The elongated body 102 is a needle 110 which comprises a hollow channel of which the exit 108 is shown. The needle may be used to implant therapeutic devices 112 into a corpus. The therapeutic device 112 may be pushed through the hollow channel of the needle with help of a plunger. The elongated body 102 further comprises an impedance sensor element 104 which is arranged at a position close to the hollow channel of the needle. The impedance sensor element 104 is coupled to wires 106 which are attached to or are provided within the needle 110. The wires 106 may be coupled to a detection device. The combination of the detection device and the impedance sensor element 104 is capable of detecting the presence of the therapeutic device 112 at a specific location (a first position) $P_1$ in the hollow channel of the needle 110. The presence of the therapeutic device 112 is detected when a signal provided by the impedance sensor element 104 changes. It is to be noted that, depending on the specific characteristics of the impedance sensor element 104 and the specific characteristics of the therapeutic device 112, the impedance of the impedance sensor element 104 may change in response to the arrival or removal of the therapeutic device 112. This means that the resistance, the capacitance and/or the impedance of the impedance sensor element 104 may change. In another example, the impedance sensor element 104 comprises a linear variable differential transformer (LVDT) which uses a transformer-action to generate a signal that changes in response to the presence of the therapeutic device 112.

In the example of FIG. 1a, the therapeutic device 112 is present at a second position $P_2$ in the hollow channel of the needle. If the therapeutic device 112 is, for example, pushed to the first position $P_1$, the signal provided by the impedance sensor 104 changes. When such a change is detected it is know that the therapeutic device is present at the first position $P_1$. During implantation of the therapeutic device 112, it is advantageous to have an independent check which confirms to the surgeon that the therapeutic device is present immediately in front of the exit 108 of the hollow channel. This provides the surgeon with location information. Based on, for example, the length of the needle which is inside the corpus, the surgeon knows at which depth below the skin the therapeutic device is going implanted if, at the moment that the therapeutic device 112 is at the first position $P_1$, the surgeon withdraws the needle while keeping the therapeutic device at its position with, for example, a plunger.

Figure 1B:
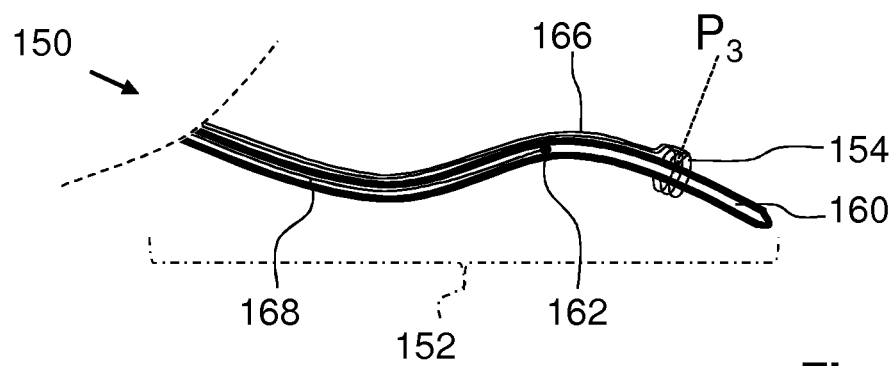

The therapeutic device may comprise energy emitting therapeutic devices that are implanted in the corpus radiate, in general, a relatively low amount of energy such that only tissues in the immediate neighborhood of the therapeutic devices are treated. In other treatments high dose energy emitting therapeutic devices are temporarily placed at a specific position in a body. The treatment device 150 of FIG. 1b is an example of treatment device which may assist a radiotherapist or surgeon to accurately place the therapeutic device at the specific position in the corpus. The therapeutic device may also be a surgical tool, such as a biopsy tool It is to be noted that the specific position $P_1$, may also be read as "the specific region" which is a region in the direct neighborhood of the impedance sensor element 104 because the signal provided by the impedance sensor element 104 may already change when a portion of the therapeutic device 112 arrives in the direct neighborhood of the impedance sensor element 104. For example, the portion of the channel which is adjacent to the impedance sensor element 104 may be the specific region.

FIG. 1b schematically shows another embodiment of a treatment device 150. FIG. 1b shows an elongated body of a catheter. Catheters are used in many medical procedures and the catheter of FIG. 1b may be used in high dose rate brachytherapy for treating prostate cancer. The catheter is, for example, inserted in the urethra until a relatively large part of the catheter is in the prostrate. Subsequently a high dose energy emitting therapeutic device 162 is fired into the hollow channel 160 of the catheter towards a specific position $P_3$ which is near the prostrate tissue to be treated (assuming that the catheter up to the required position in the urethra). Such a high dose energy emitting therapeutic device 162 is attached to a wire 168 which determines the distance the therapeutic device 162 can travel into the catheter and which is used to retract the therapeutic device 162 after a predetermined time interval. In such procedures it is very important that the therapeutic device 162 reaches the specific position $P_3$, because, otherwise, a wrong tissue is irradiated, which may damage the wrongly irradiated tissue and which decreases the efficacy of the treatment.

The treatment device 150 of FIG. 1b comprises at the specific position $P_3$ a coil 154 around the channel 160. The coil 154 is coupled to two wires 166 which may be coupled to an inductance detector. The coil 154 and the wires 166 are arranged in the material of the catheter such that they are, in use, electrically isolated from the corpus and, in an optional embodiment, they are electrically isolated from the hollow channel 160. The therapeutic device 162 comprises at least one material which influences electromagnetic fields. Such a material is, for example, a metal. If the therapeutic device 162 arrives at the specific position $P_3$, which is a position in the channel 160 where the coil 154 encloses the channel 160, the inductance of the coil 154 changes. This change of the inductance of the coil 154 is detectable by the inductance detector which is coupled to the wires 166. Checking whether the inductance of the coil 154 changes provides an independent check to the surgeon or radio therapist about the location of the therapeutic device 162. For example, if the therapeutic device 162 is shot into the channel 160, but gets stuck in the channel 160 before it reaches the specific position $P_3$, no change of inductance is detected and the surgeon or radio therapist may decide to prematurely retract the therapeutic device 162.

Figure 1C:
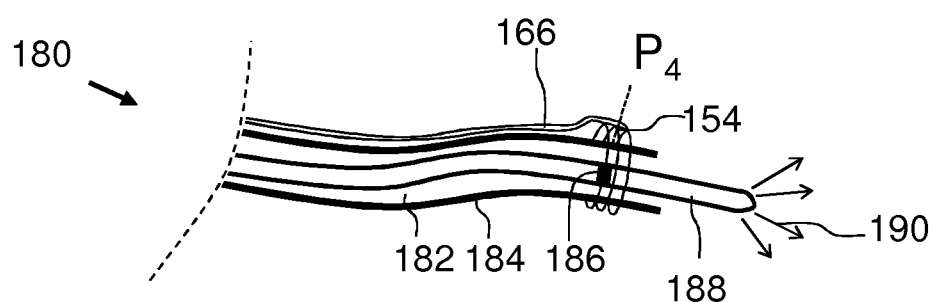

FIG. 1c schematically shows a further embodiment of a treatment device 180. The treatment device 180 also comprises an elongated body which is formed by a probe 184 which has a hollow channel 182. Around the channel of the probe 184, close to the exit of the probe, is provided a coil 154 which is coupled to wires 166 which may be used to couple the coil 154 to an inductance measurement device. The probe 184 is configured to guide an optical fiber 188 to a location in a corpus such that, when the optical fiber 188 protrudes out of the probe 184, the tissues near the end of the optical fiber 188 may be treated with light 190. The optical fiber 188 is a therapeutic device which radiates energy in the form of light 190. At a predetermined position at the optical fiber 188 is provided a metal marker 186—the metal marker 186 is, for example, arranged around the optical fiber 188. The metal marker 186 has the function of a reference element and is arranged at a predetermined distance away from the tip of the optical fiber 188 such that, when the presence of the metal marker 186 is detected by the coil 154, the optical fiber 188 protrudes for a well-known distance out of the probe 184. Thus, when the metal marker 186 is in at a specific position $P_4$ in the channel 182, the optical fiber 188 protrudes for the predetermined distance out of the probe 184. When, subsequently, a change of the inductance of the coil 154 is detected by the inductance measurement device, independently obtained information about the position of the optical fiber 188 with respect to position of the probe 184 is provided to, for example, a surgeon to assist him in deciding whether a light source must be switched on.

Figure 2:
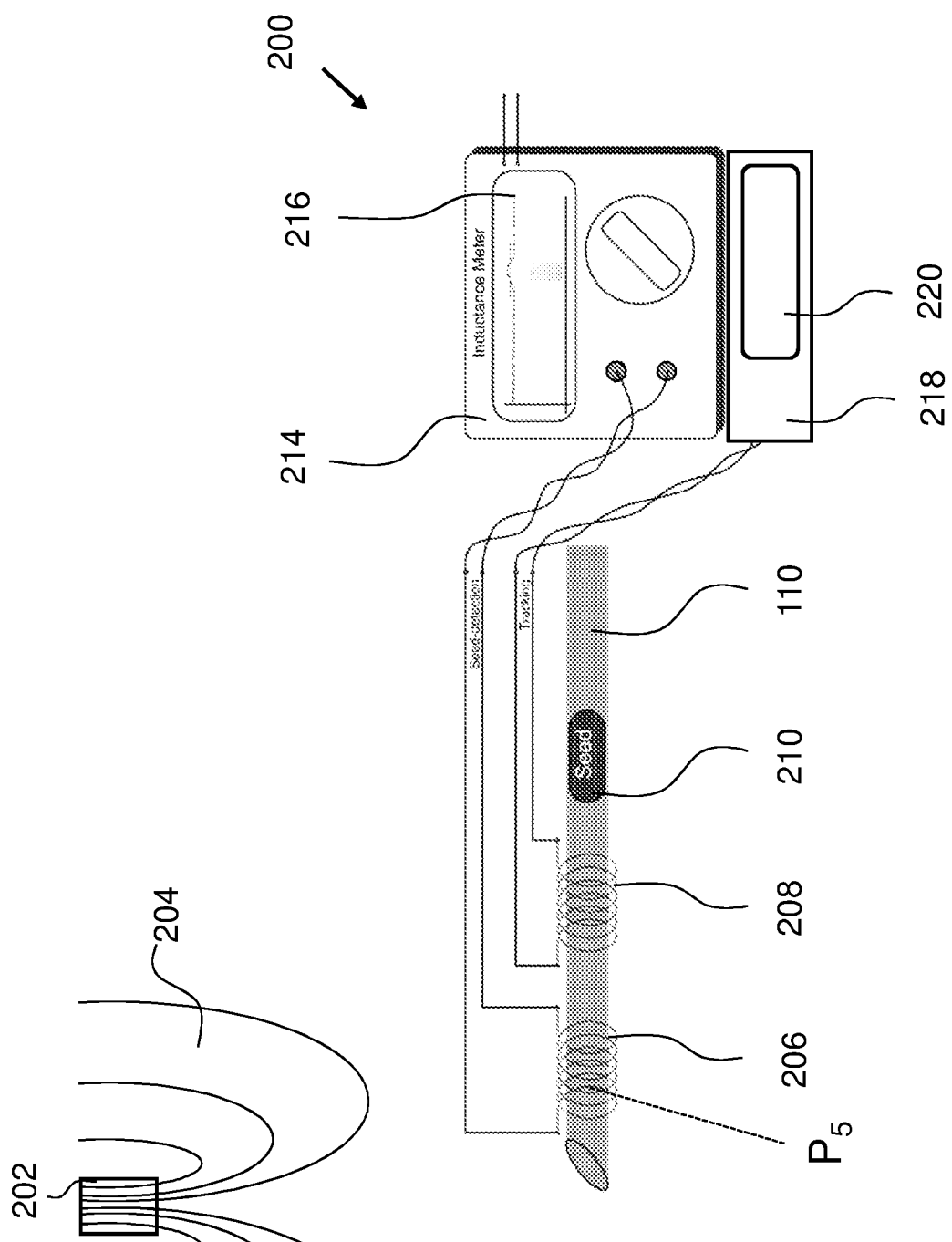

FIG. 2 schematically shows an embodiment of a treatment system 200 according to the second aspect of the invention. The treatment system 200 comprises a hollow needle 110, and an inductance measurement device 214. Optionally, the treatment system 200 comprises a tracking and imaging device 218, a field generator 202 and/or an energy emitting therapeutic device 210.

The hollow needle 110 is an elongated body which comprises a channel through which the therapeutic device 210 may be guided to a specific position $P_5$ within the hollow needle and the therapeutic device 210 may be implanted into a corpus by pushing the therapeutic device 210 out of the needle by, for example, a plunger. The hollow needle 110 comprises at the specific position $P_5$ a first coil 206 which is arranged around the channel. The first coil 206 is coupled to wires which are arranged at or within the needle. The wires are provided to couple the first coil 206 to the inductance measurement device 214. If the therapeutic device 210 arrives at the specific position $P_5$, the inductance of the coil changes and the inductance measurement device 214 detects this change and provides, for example, information to a user of the treatment system 200 on a display 216.

Around the channel of the hollow needle 110 is arranged a second coil 208. The second coil 208 is, in the example of FIG. 2, not arranged at the specific position $P_5$, however, an arrangement of the first coil 206 and the second coil 208 at the specific position $P_5$ is not excluded in the context of this document. The second coil 208 is also coupled to some wires which may be coupled to a tracking and imaging device 218 which is capable of showing on a display 220 a position of the second coil 208 with respect to a position of the field generator 202. The field generator 202 is arranged at a fixed, known position (and thus, in use, with respect to a corpus of a patient), and the field generator 202 generates a relatively strong electromagnetic field 204. The combination of the second coil 208 and tracking an imaging device 218 is capable of tracking the relative position of the second coil 208 with respect to the known position of the field generator 202 by analyzing the sensed electromagnetic field 204. These technologies are well-known in the art under the term Interventional Imaging Systems based on Electromagnetic tracking. The known tracking and imaging devices 218 are, for example, capable of showing within an earlier obtained Computed Tomography (CT) image at which position the second coil 208 is present within the corpus. Thus, the second coil 208 and the tracking and imaging device 218 may be used by a surgeon to know where the needle 110 is exactly within the corpus. The first coil 206 may be used by a surgeon to known where the therapeutic device is within the channel of the hollow needle 110. By combining this information, the surgeon knows where the therapeutic device is exactly within the corpus of the patient.

Figure 3:
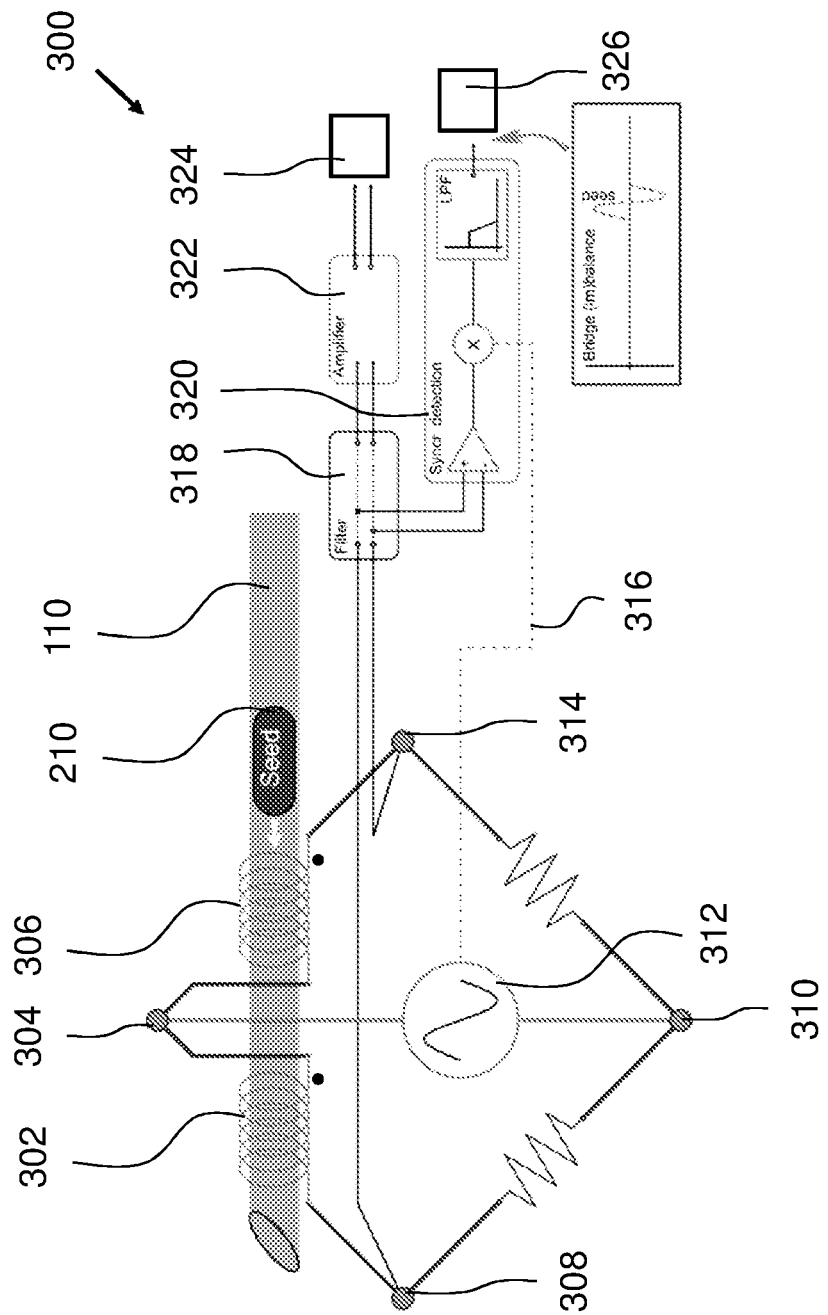

FIG. 3 schematically shows another embodiment of a treatment system 300. The treatment system 300 is similar to the treatment system 200 of FIG. 2, however, there are a number of significant differences. The treatment system 300 also comprises a hollow needle 110 which comprises a first coil 302 and a second coil 306. The hollow needle 110 comprises a channel through which an energy emitting therapeutic device 210 may be guided to a specific position within the channel or may be released into a corpus via an exit of the channel. The treatment system 300 further comprises a tracking and imaging system 324 which is similar to the previously discussed tracking and imaging system 218 of FIG. 2, and comprises an impedance detection device which comprises a synchronous detector 320 and an imaging device 326.

The first coil 302 and the second coil 306 are coupled in a so-termed bridge arrangement. In the bridge arrangement specific advantageous effects may be obtained which are explained hereinafter. The first coil 302 and the second coil 306 are arranged in a series arrangement. A first terminal is defined by the point where the first coil 302 is coupled to the second coil 306. The first coil 302 is coupled between the first terminal 304 and a second terminal 308. The second coil 306 is coupled between the first terminal and a third terminal 314. A series arrangement of a first load resistor $R_{L1}$ and a second load resistor $R_{L2}$ is coupled between the second terminal 308 and the third terminal 314. A common terminal in between the first load resistor $R_{L1}$ and a second load resistor $R_{L2}$ forms a fourth terminal 310. In between the first terminal 304 and the fourth terminal 310 is arranged an excitation source 312 which provides an AC signal to the bridge configuration. The AC signal is, for example, a sine waveform, a saw tooth waveform, a square waveform, a triangle waveform or another waveform which causes the flow of an alternating current. The most important characteristic of the AC signal is that it generates an alternating current through the first coil 302 and the second coil 306. In an example, the AC signal is a 100 kHz signal with an amplitude of 1 Volts peak-to-peak ($V_{pp}$). The power provided by the excitation source 312 is divided into two portions and is provided, based on the resistance of the load resistors $R_{L1}$, $R_{L2}$ and the impedance of the coils 302, 306, in equal portions to the first coil 302 and to the second coil 306. The first coil 302 and the second coil 306 generate a magnetic field which may be influenced by the therapeutic device 210. When the therapeutic device arrives in the second coil 306, the impedance of the second coil changes and, thus, a value of a current flowing through the second coil 306 changes. When the therapeutic device moves from the second coil 306 to the first coil 302, the impedance of the second coil 306 returns to its normal level and the impedance of the first coil 302 changes resulting in a change of a current flowing through the first coil 302. These changes of currents through the second coils 306 and through the first coil 302 result in different AC voltage levels at the second terminal 308 and the third terminal 314. Furthermore, the series arrangement of the coils 302, 306 may intercept other electromagnetic fields such as an electromagnetic field generated by a field generator (not shown) which is positioned at a fixed position with respect to hollow needle 110. Those intercepted signal also induce a signal on the second terminal 308 and the third terminal 314.

The second terminal 308 and the third terminal 314 are coupled to the detection devices which are introduced above. The signal obtained from these two terminals 308, 314 is first provided to an optional filter 318 which splits the signal intended for the inductance detection into a first filtered signal and filters the signal intended for the tracking and imaging device into a second filtered signal. The filter comprises, for example, band filters which let through specific frequencies which relates to the frequency of the excitation source 312 and which relates to the frequency of the field generator. The first filtered signal is provided to the synchronous detector. The second filtered signal is optionally amplified by an amplifier 322 and is provided to the tracking and imaging device 324. In other embodiment, the signal provided by the two terminals 308, 314 is directly provided to the tracking and imaging system 324 and the synchronous detector 320 if these detection devices are capable of distinguishing between the different frequencies of the excitation source 312 and the field generator.

The synchronous detector 320 receives also a signal from the excitation source 312 and this signal is used to synchronously detect the signal received from the bridge configuration such that voltage differences of an AC signal at the second and third terminals 308, 314 are detected and provided, usually, as a low frequency signal (related to the moving speed of the therapeutic device 210) to an imaging device 326. The signal, which is provided by the synchronous detector 320, is a signal which is centered around 0 volts. When the therapeutic device moves through the second coil 306, the voltage of the signal becomes ether positive or negative. When the therapeutic device moves through the first coil 302, the signal becomes an opposite voltage compared to the situation that the therapeutic device moves through the second coil 306. Synchronous detection inherently rejects information at all frequencies (and optionally even phases) other than the frequency (and phase) of the excitation source 312. This offers, in specific applications a perfect rejection of other electromagnetic signals being presents in the environment of the treatment system 300.

It is to be noted that the excitation source 312 and the load resistors $R_{L1}$, $R_{L2}$ are drawn in the immediate neighborhood of the needle 110. In a practical embodiment, three wires are coupled to the coils 302, 306 and the wires are provided at the surface of, or within, the needle and the excitation source 312 and the load resistors $R_{L1}$, $R_{L2}$ are coupled to the wires in accordance with the drawn schematic. Thus, the treatment system 300 is arranged such that the voluminous components are, in use, arranged outside the corpus of the patient. It is further to be noted that, in an optional embodiment, the first coil 302 and the second coil 306 are coupled to each other in an additive arrangement, which means, their winding directions are in the same direction. This allows a better detection of the external electromagnetic field.

Figure 4:
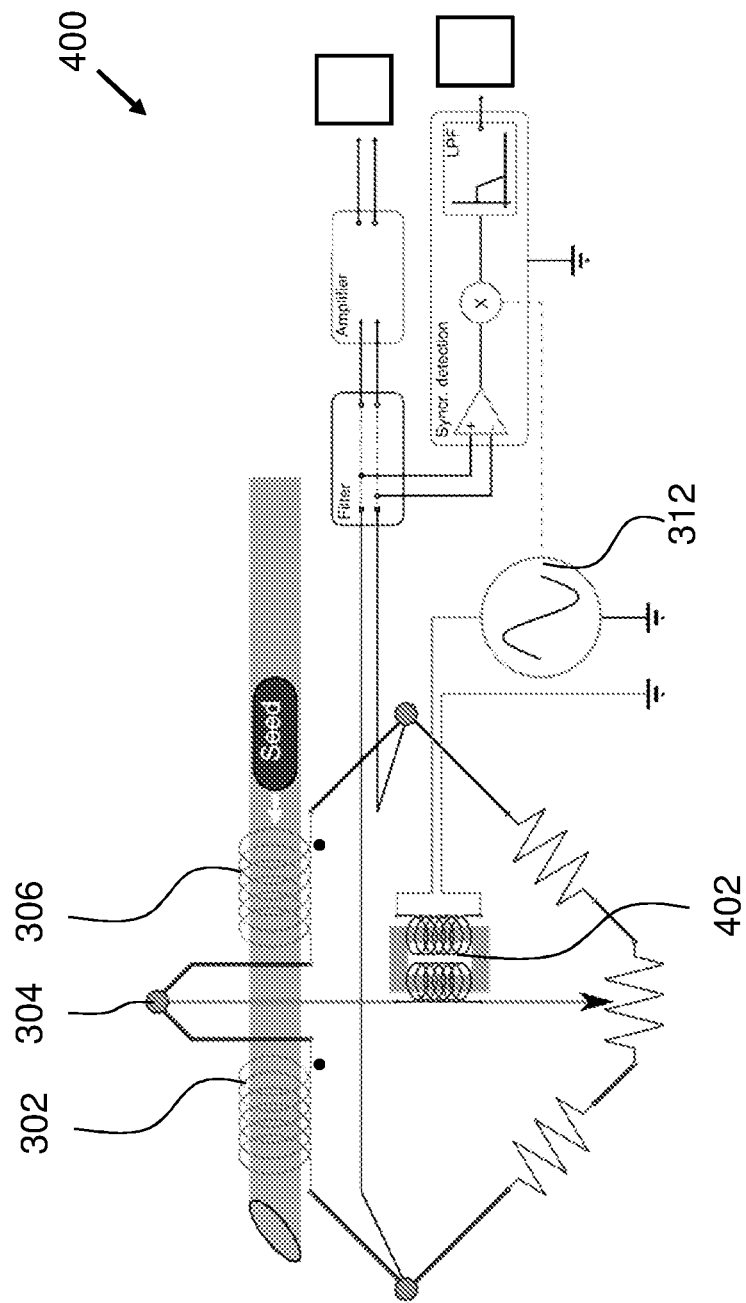

FIG. 4 schematically shows a further embodiment of a treatment system 400. Treatment system 400 is similar to treatment system 300 of FIG. 3. However, in the treatment system 400, the excitation source 312 is electrically isolated from the components which are, in use, inserted into the corpus. The signal of the excitation source 312 is provided to the bride configuration via a transformer 402. Additionally, in between the first load resistor $R_{L1}$ and the second load resistor $R_{L2}$ is provided a balancing resistor $R_B$, which may be a potentiometer which may be used to balance the current provided to the two branches of the bridge configuration. The transformer 402 is coupled in between the first terminal and a movable contact of the balancing resistor $R_B$. The balancing resistor $R_B$ may be used to create a balance in the bridge-configuration if the coils 302, 306 and/or the load resistors $R_{L1}$, $R_{L2}$ are not exactly balanced.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A treatment system for treating a part of a corpus of a living being, the treatment system comprising:
   a treatment device for temporarily or permanently placing a therapeutic device in a part of a corpus of a living being, the treatment device comprising an elongated body for being inserted in the part of the corpus, the elongated body comprising: a channel for guiding the therapeutic device to a specific position within the channel, and/or for holding the therapeutic device at the specific position within the channel; and an impedance sensor element configured to be coupled to a detection device for detecting a presence of the therapeutic device at the specific position based on a change of a signal provided by the impedance sensor element;
   a detection device connectable to the impedance sensor element of the treatment device for detecting a change of the signal provided by the impedance sensor element in response to the presence of the therapeutic device at the specific position; and
   a tracking device connectable to the impedance sensor element of the treatment device for tracking a relative position of the impedance sensor element with respect to a field generator, which is arranged at a fixed position with respect to the corpus, wherein the field generator generates an electromagnetic field, which is detectable by the impedance sensor element.

2. The treatment system according to claim 1, wherein the impedance sensor element comprises a coil for detecting an electromagnetic field at the specific position.

3. The treatment system according to claim 2, wherein the coil is arranged around the channel.

4. The treatment system according to claim 1, wherein the elongated body comprises a needle, probe, a trocar, a cannula or a catheter.

5. The treatment system according to claim 1, wherein the elongated body comprises a further impedance sensor element being configured to be coupled to the detection device for detecting, in collaboration with a detection via the impedance sensor element, the presence of the therapeutic device at the specific position based on a change of a signal provided by the impedance sensor element, and/or provided by the further impedance sensor element.

6. The treatment system according to claim 5, wherein the further impedance sensor element comprises a further coil being arranged around the channel for detecting the electromagnetic field at the specific position.

7. The treatment system according to claim 5, wherein at least one of the impedance sensor element and the further impedance sensor element is configured to detect an electromagnetic field being generated by a field generator, which is arranged at a fixed position with respect to the corpus, and the tracking device is connectable to the further impedance sensor element.

8. A treatment system according to claim 5, further comprising an excitation source for generating an AC voltage, wherein the impedance sensor element, the further impedance sensor element and the excitation source are arranged in a bridge configuration, the bridge configuration comprises:

a first terminal, a second terminal, a third terminal and a fourth terminal, a first load resistor being arranged between the second terminal and the fourth terminal, a second load resistor being arranged between the third terminal and the fourth terminal, the second load resistor, and the first load resistor are configured to balance a load of each one of two current conduction paths of the bridge configuration, wherein the excitation source is arranged between the first terminal and the fourth terminal, the impedance sensor element is arranged between the first terminal and the second terminal, the further impedance sensor element is arranged between the first terminal and the third terminal, and the second terminal and the third terminal are for being coupled to one or more detection devices.

9. The treatment system according to claim 1, wherein the therapeutic device comprises an optical fiber for guiding light into the part of the corpus, the optical fiber comprising a reference element arranged at a predefined position at the optical fiber, and wherein the impedance sensor element is configured to detect the presence of the reference element at the specific position.

10. The treatment system according to claim 1, further comprising the therapeutic device.

11. The treatment system according to claim 1, wherein the therapeutic device is an energy emitting therapeutic device.

12. The treatment system according to claim 11, further comprising low-dose rate therapeutic seeds.

13. The treatment system according to claim 1, wherein the impedance sensor element comprises a linear variable differential transformer.

* * * * *